US011771320B2

(12) United States Patent
Georgiev et al.

(10) Patent No.: US 11,771,320 B2
(45) Date of Patent: Oct. 3, 2023

(54) SYSTEM AND METHOD FOR AUGMENTING PATIENT-TECHNOLOGIST COMMUNICATION

(71) Applicant: GE Precision Healthcare LLC, Wauwatosa, WI (US)

(72) Inventors: Emil M. Georgiev, Hartland, WI (US); Erik P. Kemper, Franklin, WI (US)

(73) Assignee: GE Precision Healthcare LLC, Wauwatosa, WI (US)

(*) Notice: Subject to any disclaimer, the term of this patent is extended or adjusted under 35 U.S.C. 154(b) by 152 days.

(21) Appl. No.: 17/004,994

(22) Filed: Aug. 27, 2020

(65) Prior Publication Data

US 2022/0061664 A1    Mar. 3, 2022

(51) Int. Cl.
| | |
|---|---|
| *A61B 5/00* | (2006.01) |
| *A61B 5/055* | (2006.01) |
| *G06F 40/58* | (2020.01) |
| *G16H 10/60* | (2018.01) |
| *A61B 5/1171* | (2016.01) |

(52) U.S. Cl.
CPC ............ *A61B 5/002* (2013.01); *A61B 5/0046* (2013.01); *A61B 5/055* (2013.01); *A61B 5/1176* (2013.01); *A61B 5/7405* (2013.01); *A61B 5/7435* (2013.01); *G06F 40/58* (2020.01); *G16H 10/60* (2018.01)

(58) Field of Classification Search
CPC ....... A61B 5/002; A61B 5/0046; A61B 5/055; A61B 5/1176; A61B 5/7405; A61B 5/7435; G06F 40/58; G16H 10/60
See application file for complete search history.

(56) References Cited

U.S. PATENT DOCUMENTS

| | | | |
|---|---|---|---|
| 6,468,212 B1* | 10/2002 | Scott ...................... | A61B 8/463 600/440 |
| 8,214,012 B2 | 7/2012 | Zuccolotto | |
| 9,244,139 B2 | 1/2016 | Brown | |
| 2002/0164054 A1* | 11/2002 | Mccartney ............. | G06V 40/16 382/118 |
| 2005/0283068 A1* | 12/2005 | Zuccolotto ............. | A61B 5/055 600/410 |

(Continued)

OTHER PUBLICATIONS

Acuff et al.; Reduction of patient anxiety in PET/CT imaging by improving communication between patient and technologist; Journal of Nuclear Medical Technology; Sep. 2014;42(3):211-7; [http://tech.snmjournals.org/content/42/3/211 .short]; 8 pages.

(Continued)

*Primary Examiner* — Nabil H Syed
*Assistant Examiner* — Cal J Eustaquio

(57) ABSTRACT

The present disclosure relates to a system and method for augmenting patient-technologist communication, before, during, and after a medical imaging procedure. In accordance with certain embodiments, a system includes a processor and a computer readable storage medium in communication with the processor. The processor executes program instructions stored in the computer readable storage medium which cause the computer processor to generate media that relates to a medical imaging procedure as a function of information in an electronic medical record that corresponds to a patient and output the media that relates to a medical imaging procedure to a display or a speaker.

3 Claims, 7 Drawing Sheets

(56) References Cited

U.S. PATENT DOCUMENTS

| | | | | |
|---|---|---|---|---|
| 2007/0055550 | A1* | 3/2007 | Courtney | G16H 70/20 |
| | | | | 235/375 |
| 2007/0102672 | A1* | 5/2007 | Hamilton | C04B 35/195 |
| | | | | 252/478 |
| 2010/0180029 | A1* | 7/2010 | Fourman | G06F 16/9535 |
| | | | | 709/225 |
| 2011/0257509 | A1* | 10/2011 | Olsen | A61N 1/37235 |
| | | | | 600/411 |
| 2013/0297219 | A1* | 11/2013 | Bangera | G16H 50/30 |
| | | | | 702/19 |
| 2015/0245166 | A1* | 8/2015 | Lee | H04W 4/80 |
| | | | | 455/41.2 |
| 2015/0278483 | A1* | 10/2015 | Pruitt | G16H 10/60 |
| | | | | 705/3 |
| 2017/0311842 | A1* | 11/2017 | Boettger | A61B 6/0407 |
| 2019/0150876 | A1* | 5/2019 | Kagermeier | A61B 6/06 |

OTHER PUBLICATIONS

Ajam et al.; Effects of Interpersonal Skills Training on MRI Operations in a Saturated Market: A Randomized Trial; Journal of American College of Radiology; Jul. 2017; vol. 14, Issue 7; pp. 963-970; https://www.jacr.org/article/S1546-1440(17)30323-X/pdf; 16 pages.

GE Healthcare; 7 Ways Technologists Can Reduce Patient Anxiety During CT Scans; May 16, 2019; https://www.gehealthcare.com/long-article/7-ways-technologists-can-reduce-patient-anxiety-during-ct-scans; 5 pages.

Siwicki; University tests AI-powered radiology assistant; Healthcare IT News; Jan. 3, 2020; https://www.healthcareitnews.com/news/university-tests-ai-powered-radiology-assistant; 7 pages.

\* cited by examiner

SYSTEM AND METHOD FOR AUGMENTING PATIENT-TECHNOLOGIST COMMUNICATION

TECHNICAL FIELD

This disclosure relates to a system and method for augmenting patient-technologist communication, and more particularly, to a system and method for augmenting patient-technologist communication before, during, and after a medical imaging procedure.

BACKGROUND

In order to visualize internal structures, a physician may order a patient undergo various medical imaging procedures. In order to obtain quality images, a technologist instructs the patient to perform various tasks. Before the imaging procedure, the technologist may instruct the patient to change into a medical gown. After the patient changes, the technologist may further instruct the patient to orient themselves in a particular manner relative to a medical imaging device (i.e., computed tomography (CT) imaging system, a magnetic resonance imaging (MRI) system, a positron emission tomography (PET) imaging system, an X-ray imaging system, and hybrids thereof, such as a PET/CT imaging system or a PET/MR imaging system, etc.). Prior to the imaging procedure, a technologist or other medical professional may communicate with the patient to prepare them for the procedure, properly position the patent on the imaging system, and answer any questions they may have. During the imaging procedure, the technologist may communicate with the patient in order to adjust various imaging parameters. For example, a CT scan of the chest may require a patient to hold their breath as movement from breathing can blur the images. Accordingly, the technologist may ask the patient how long they can hold their breath and may change image acquisition times based on the patient's answer. After the imaging procedure, the technologist and patient may communicate with the patient to schedule a follow up appointment to review the captured medical images with a physician.

SUMMARY

In one embodiment, the present disclosure provides a system. The system comprises a processor and a computer readable storage medium in communication with the processor. The processor executes program instructions stored in the computer readable storage medium which cause the computer processor to generate media that relates to a medical imaging procedure as a function of information in an electronic medical record that corresponds to a patient and output the media that relates to a medical imaging procedure to a display or a speaker.

In another embodiment, the present disclosure provides a system. The system comprises a processor and a computer readable storage medium in communication with the processor. The processor executes program instructions stored in the computer readable storage medium which cause the computer processor to cause an imaging device to start an imaging procedure according to an imaging protocol, determine an imaging parameter as a function of biometric data or audio that relates to the imaging parameter, and set an imaging parameter of the imaging protocol to the determined imaging parameter.

In yet another embodiment, the present disclosure provides a system. The system comprises a processor of a node of a cloud computing environment and a computer readable storage medium in communication with the processor. The processor executes program instructions stored in the computer readable storage medium which cause the computer processor to generate a graphical user interface comprising: a plurality of icons that each correspond to a media file stored in a computer readable storage medium, wherein each icon displays information or an instruction relating to a medical imaging procedure, and wherein the media file includes information or instructions that corresponds to the displayed information or instruction, output the graphical user interface to a first display, and output the media file that corresponds to an icon to a second display or a speaker in response to a technologist selecting the icon.

BRIEF DESCRIPTION OF THE DRAWINGS

Various aspects of this disclosure may be better understood upon reading the following detailed description upon reference to the drawings in which.

Figure 1:
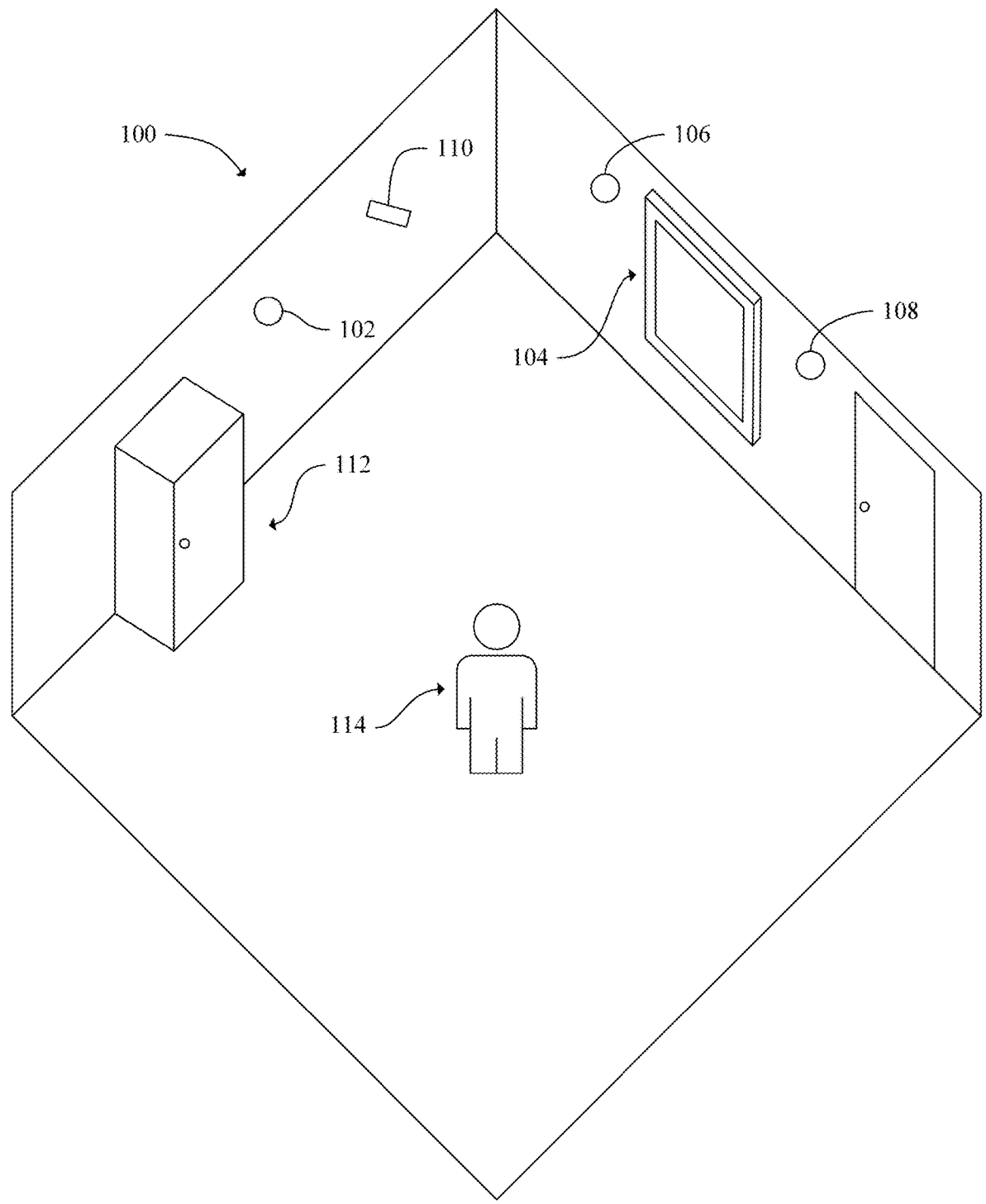
FIG. 1 depicts a changing room in accordance with an exemplary embodiment.

The drawings illustrate specific aspects of the described components, systems, and methods for augmenting patient-technologist communication. Together with the following description, the drawings demonstrate and explain the principles of the structures, methods, and principles described herein. In the drawings, the thickness and size of components may be exaggerated or otherwise modified for clarity. Well-known structures, materials, or operations are not shown or described in detail to avoid obscuring aspects of the described components, systems, and methods.

DETAILED DESCRIPTION

One or more specific embodiments of the present disclosure are described below in order to provide a through understanding. These described embodiments are only examples of the systems and methods for augmenting patient-technologist communication. The skilled artisan will understand that specific details described in the embodiments can be modified when being placed into practice without deviating from the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (i.e., a material, element, structure, number, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

Referring to the figures generally, the present disclosure describes systems and methods for augmenting patient-technologist communication. Some embodiments the present disclosure describe systems and methods that implement a virtual assistant for augmenting patient-technologist communication.

Before, during, and after a medical imaging procedure a technologist may have to perform various tasks that require their attention. A patient undergoing a medical imaging procedure may be unfamiliar with the process and may have questions for the technologist. The technologist may not have the time or inclination to answer the patient's question. Some embodiments of the present disclosure provide a computer program that can perform various tasks for the technologist (a "virtual assistant"). The tasks may include automatically answering patient questions on behalf of the technologist. Providing a virtual assistant that automatically answers patient questions on behalf of the technologist may allow the technologist to focus on other tasks that require their attention. Furthermore, providing a virtual assistant enables the imaging procedure to be contactless when the patient is ambulatory. Providing a contactless imaging procedure may aid in reducing the spread of infectious diseases (i.e., Corona Virus Disease 2019 (COVID-19)).

Other embodiments of the present disclosure may provide a graphical user interface (GUI) of a computer system that presents the technologist with common answers to patient questions and/or common patient instructions. The technologist may select the answer/instructions which causes the computer system to provide an answer/instruction to the patient. Providing a GUI that enables a technologist to cause a computer system to provide an answer/instruction to the patient may save the technologist time in providing an answer/instruction to the patient thereby allowing the technologist to return to other tasks that require their attention.

Medical imaging procedures rely on patient-technologist communication in order to obtain high quality images. When a medical imaging procedure includes exposing the patient to radiation, a breakdown in patient-technologist communication may lead to unnecessary radiation exposure. For example, a CT scan may require a patient to lay still as any movement may blur the images. In this example, the patient may not speak the same language as the technologist or may not be able to hear the technologist causing the patient to misunderstand the technologist's instructions. As a result, the patient may move too soon thereby blurring the images. Accordingly, the patient may have to undergo a second CT scan which exposes them to additional radiation.

Some embodiments of the present disclosure include a multilingual virtual assistant that communicates with the patient in a language chosen by the patient. Providing a virtual assistant that communicates in a language chosen by the patient may increase the patient's ability to communicate with the technologist and/or may increase the patient's ability to understand various instructions from the technologist. Other embodiments of the present disclosure provide a virtual assistant that displays text and/or plays audio to the patient. Providing a virtual assistant that displays text and/or plays audio to the patient may increase the patient's ability to communicate with the technologist and/or may increase the patient's ability to understand various instructions from the technologist.

Furthermore, the quality of a medical image is related to imaging parameters. For example, an image acquisition period that is too long may cause the medical imaging device to produce inadequate medical images if the patient begins to move during acquisition. Some embodiments of the present disclosure include a virtual assistant that automatically adjusts imaging parameters. Providing a virtual assistant that automatically adjusts imaging parameters may provide more adequate medical images.

Referring now to FIG. 1, a changing room 100 is shown in accordance with an exemplary embodiment. As illustrated in FIG. 1, in some embodiments, the changing room 100 includes a first sensor 102, a first display 104, a first speaker 106, a first microphone 108, a first projector 110, and a changing closet 112.

The first sensor 102 may be any sensor capable of determining a patient 114 has entered the changing room 100 (i.e., a camera, a motion detector, a pressor sensor, a heat detector, etc.). The first display 104 may be any display capable of displaying media. In one embodiment, the first display 104 may be a projector screen. In this embodiment, the first projector 110 projects media onto the first display 104. As used herein, media includes any means of communication (i.e., audio, video, text, images, etc.).

While the first sensor 102, the first speaker 106, and the first microphone 108 are depicted on walls of the changing room 100, these devices may be anywhere in the changing room 100 (i.e., in a wall, in or on the ceiling, in or on the floor, etc.). For example, when the first sensor 102 is a pressure sensor, the first sensor 102 may be in the floor of the changing room 100. Furthermore, while the first sensor 102, the first display 104, the first speaker 106, the first microphone 108, and the first projector 110 are depicted as separate devices, at least two of these devices may be in or on the same device. In one example, the first speaker 106 and the first microphone 108 may be within the first projector 110. In another example, the first sensor 102 may be located within the first display 104. Furthermore, the first sensor 102, the first display 104, first speaker 106, first microphone 108, and the first projector 110 may be connected to one or more same or different networks (i.e., local area network (LAN), general wide area network (WAN), public network (i.e., Internet)), etc.).

Figure 2:
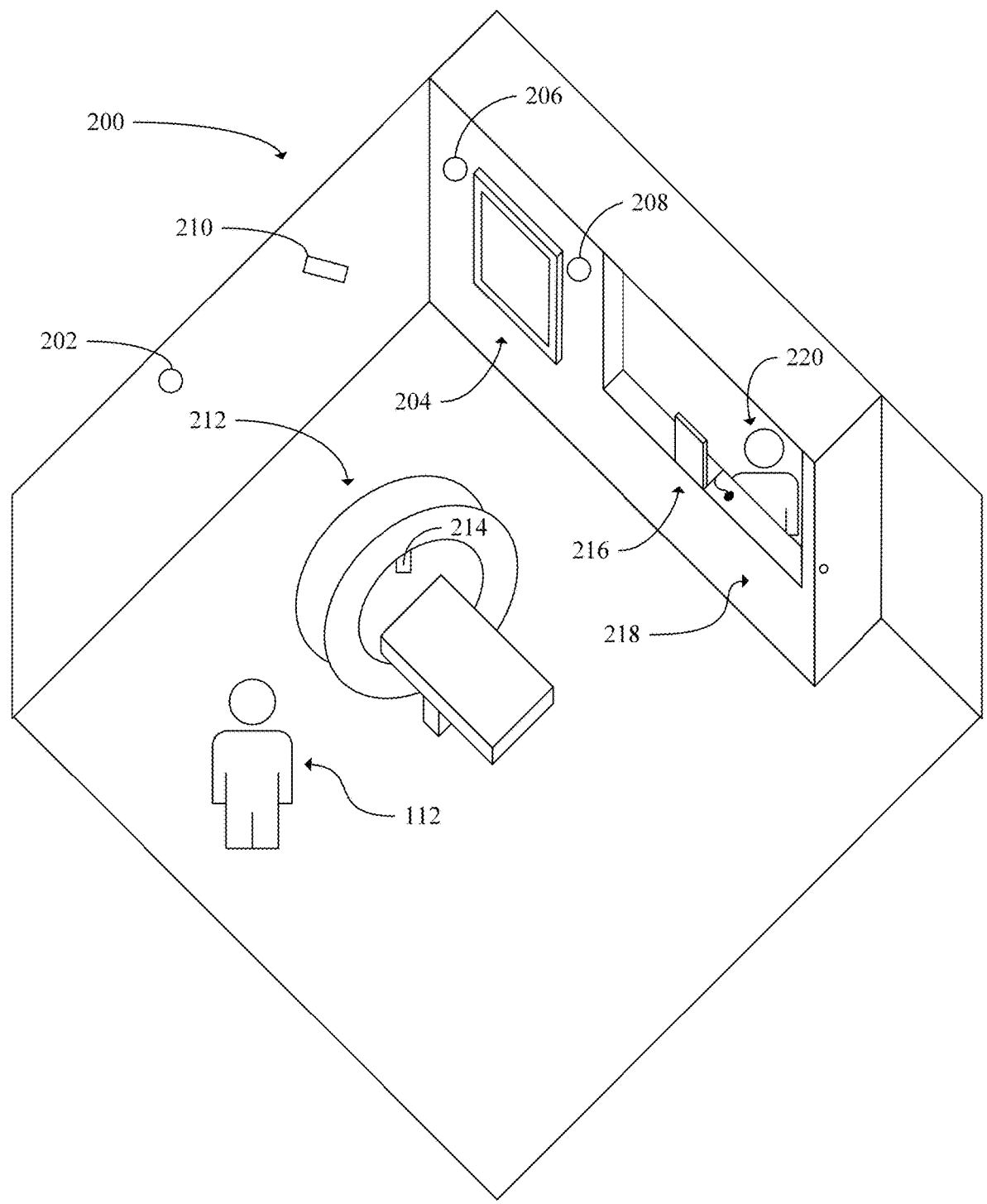
FIG. 2 depicts an imaging room in accordance with an exemplary embodiment.

Referring now to FIG. 2, an imaging room 200 is shown in accordance with an exemplary embodiment. As illustrated in FIG. 2, in some embodiments, the imaging room 200 includes a second sensor 202, a second display 204, a second speaker 206, a second microphone 208, a second projector 210, an imaging device 212, a third sensor 214, a computer system 216, and a physical barrier 218.

The second sensor 202 may be any sensor capable of determining the patient 114 has entered the imaging room 200 (i.e., a camera, a motion detector, a pressor sensor, a heat detector, etc.). The second display 204 may be any display capable of displaying media. In one embodiment, the second display 204 may be a projector screen. In this embodiment, the second projector 210 projects media onto the second display 204. The imaging device 212 may be any imaging device capable of producing medical images (i.e., computed tomography (CT) imaging system, a magnetic resonance imaging (MRI) system, a positron emission tomography (PET) imaging system, an X-ray imaging system, and hybrids thereof, such as a PET/CT imaging system or a PET/MR imaging system, etc.). While the imaging device 212 is depicted as including a cylindrical bore, in some embodiments the imaging device 212 may not include a bore. For example, the imaging device 212 may be attached to a moveable extension arm in the imaging room 200. The third sensor 214 may be any sensor capable of capturing biometric data (i.e., temperature, blood pressure, pulse, breathing rate, facial expressions, etc.) including, but not limited to, an electrocardiogram (ECG) machine, a vital sign monitor, a camera, etc. The third sensor 214 may or may not be attached to the patient 114 while the imaging procedure is in progress. The computer system 216 may be any computing device/system (i.e., tablet, personal computer, laptop, network computer, etc.) capable of controlling the imaging device 212 and operable by a technologist 220. The computer system 216 may be located behind the physical barrier 218 thereby protecting the technologist 220 from radiation emitted by the imaging device 212 while the technologist 220 operates the computer system 216.

While the second sensor 202, the second display 204, the second speaker 206, and the second microphone 208 are depicted on walls of the imaging room 200, these devices may be anywhere in the imaging room 200 (i.e., in a wall, in or on the ceiling, in or on the floor, etc.). Furthermore, while the second sensor 202, the second display 204, the second speaker 206, the second microphone 208, the second projector 210, and the imaging device 212 are depicted as separate devices, at least two of these devices may be located in or on the same device. For example, the second display 204 may be located on a surface of the imaging device 212 such that the display 204 is viewable from a bed of the imaging device 212.

The second sensor 202, the second display 204, the second speaker 206, the second microphone 208, the second projector 210, the imaging device 212, the third sensor 214, and the computer system 216 may be connected to one or more same or different networks (i.e., LAN, WAN, public network, etc.). The second sensor 202, the second display 204, the second speaker 206, the second microphone 208, the second projector 210, the imaging device 212, the third sensor 214, the computer system 216, and the projector 218 may be connected to the same network as the first sensor 102, the first display 104, first speaker 106, first microphone 108, and the first projector 110.

Figure 3:
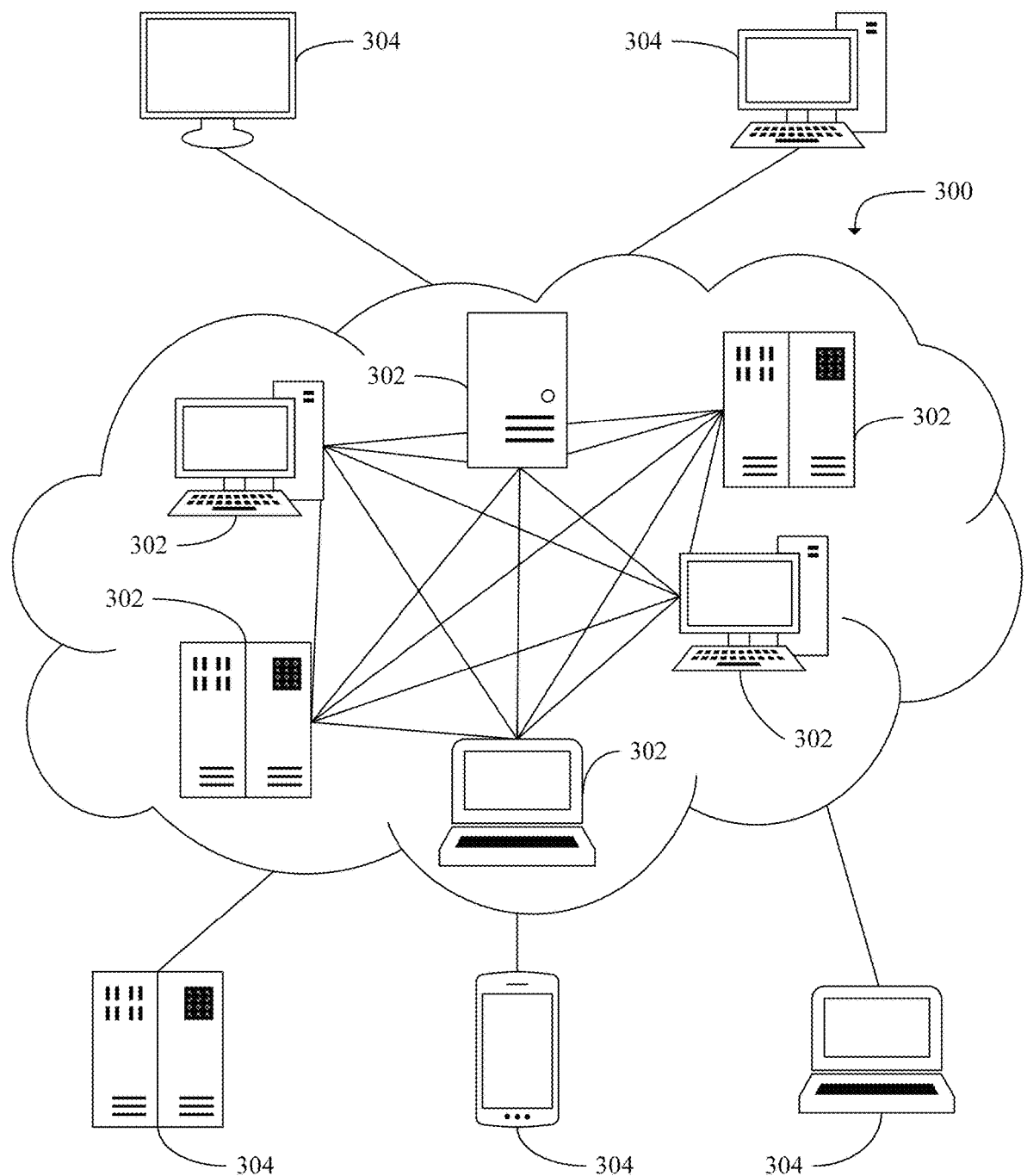
FIG. 3 is a schematic diagram of a cloud computing environment in accordance with an exemplary embodiment.

Referring now to FIG. 3, a cloud computing environment 300 is shown in accordance with an exemplary embodiment. As illustrated in FIG. 3, in some embodiments, the cloud computing environment 300 includes one or more nodes 302. Each node 302 may include a computer system/server (i.e., a personal computer system, a server computer system, a multiprocessor system, a mainframe computer system, etc.). The nodes 302 may communicate with one another and may be grouped into one or more networks.

As further illustrated in FIG. 3, one or more devices 304 may be connected to the cloud computing environment 300. The devices 304 may include the first sensor 102, the first display 104, the first speaker 106, the first microphone 108, the first projector 110, the second sensor 202, the second display 204, the second speaker 206, the second microphone 208, the second projector 210, the imaging device 212, the third sensor 214, and the computer system 216. The devices 304 may further include devices used by cloud consumers (i.e., desktop, laptop, tablet, smart phone, etc.). The devices 304 may be connected to a same or different network (i.e., LAN, WAN, public network, etc.). One or more nodes 302 may communicate with the devices 304 thereby allowing the nodes 302 to provide software services to the devices 304.

In some embodiments, a node 302 and/or a device 304 may include a storage medium that stores an electronic medical record (EMR) database and/or a picturing archiving and communications system (PACS). An EMR database includes individual EMRs that correspond to an individual patient. Each EMR includes information (i.e., age, gender, height, weight, birthdate, social security number, patient identification number, demographic information, images, medical history, diagnoses, medications, allegories, lab results, physician orders, etc.) for a corresponding patient. The EMR database and EMRs may be accessed by the nodes 302 and devices 304. A node 302 and/or device 304 that stores the PACS is connected to the imaging device 212. A PACS stores image data that is generated by the imaging device 212 and other imaging devices. The PACS and image data may be accessed by nodes 302 and devices 304.

In other embodiments, a node 302 and/or a device 304 may include a storage medium that stores one or more editable schedules. An editable schedule may include, but is not limited to, schedules for physicians of a healthcare network and medical procedure schedules (i.e., operation days/times, physical therapy days/times, imaging procedure days/times, etc.). The schedules may be accessed and/or edited by nodes 302 and/or devices 304.

Figure 4:
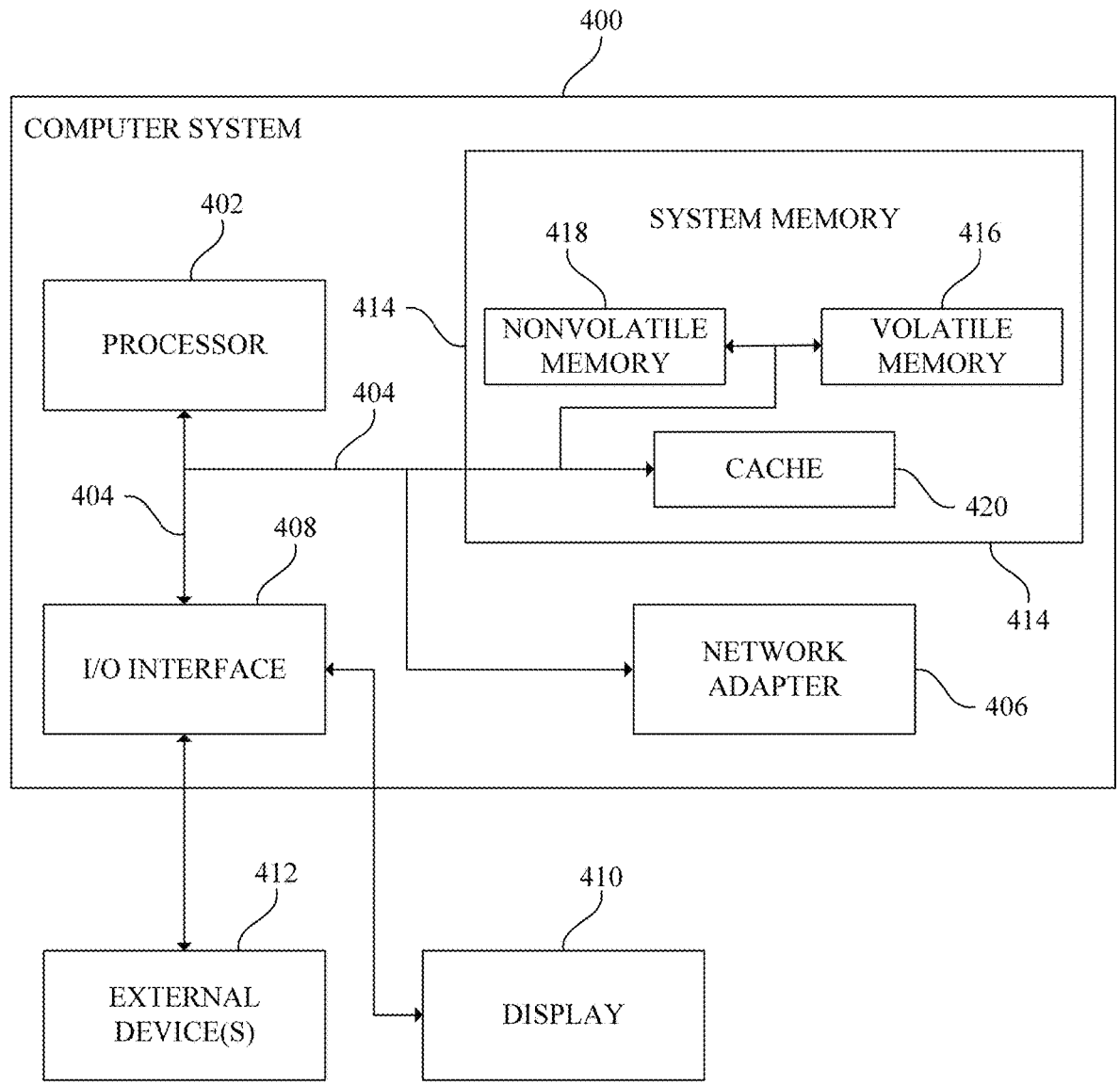
FIG. 4 is a schematic diagram of a computer system in accordance with an exemplary embodiment.

Referring now to FIG. 4, a computer system 400 is shown in accordance with an exemplary embodiment. The computer system 400 may function as the computer system 216 and/or a node 302. As illustrated in FIG. 4, in some embodiments, the computer system 400 includes a processor 402, a bus 404, a network adapter 406, an input/output (I/O) interface 408, a display 410, one or more external devices 412, and system memory 414.

The bus 404 couples the processor 402, the network adapted 406, the I/O interface 408, and the system memory 414 as shown in FIG. 4. Particularly, the bus 404 couples the processor 402 to the system memory 414. The bus 404 represents one or more of any type of bus structure (i.e., memory bus or controller, a peripheral bus, an accelerated graphics port, etc.). The computer system 400 may be connected to one or more networks (i.e., LAN, WAN, public network, etc.) via the network adapter 406. The one or more external devices 412 may include devices that allow the technologist 220 or another user to interact with/operate the computer system 400. Devices that allow the technologist 220 or another user to interact with/operate the computer system 400 include, but are not limited to, a mouse, a keyboard, a speaker, and a microphone.

The system memory 414 is a computer readable storage medium. A computer readable storage medium can be any device that can store computer readable program instructions for execution by a processor. As used herein, a computer readable storage medium is not construed as being transitory per se. The computer readable program instructions include programs, logic, data structures, etc. that when executed by the processor 402 create a means for implementing functions/acts specified in FIGS. 5A, 5B and 7. The computer readable program instructions when stored in a computer readable storage medium and executed by the processor 402 direct the computer system 400 and/or another device to function in a particular manner such that the computer readable storage medium comprises an article of manufacture. The system memory 414 may include volatile memory 416 (i.e., random access memory (RAM), etc.) and nonvolatile memory 418 (i.e., flash memory, read-only memory (ROM), magnetic computer storage devices, etc.). In some embodiments the system memory 414 may further include cache 420.

Figure 5A:
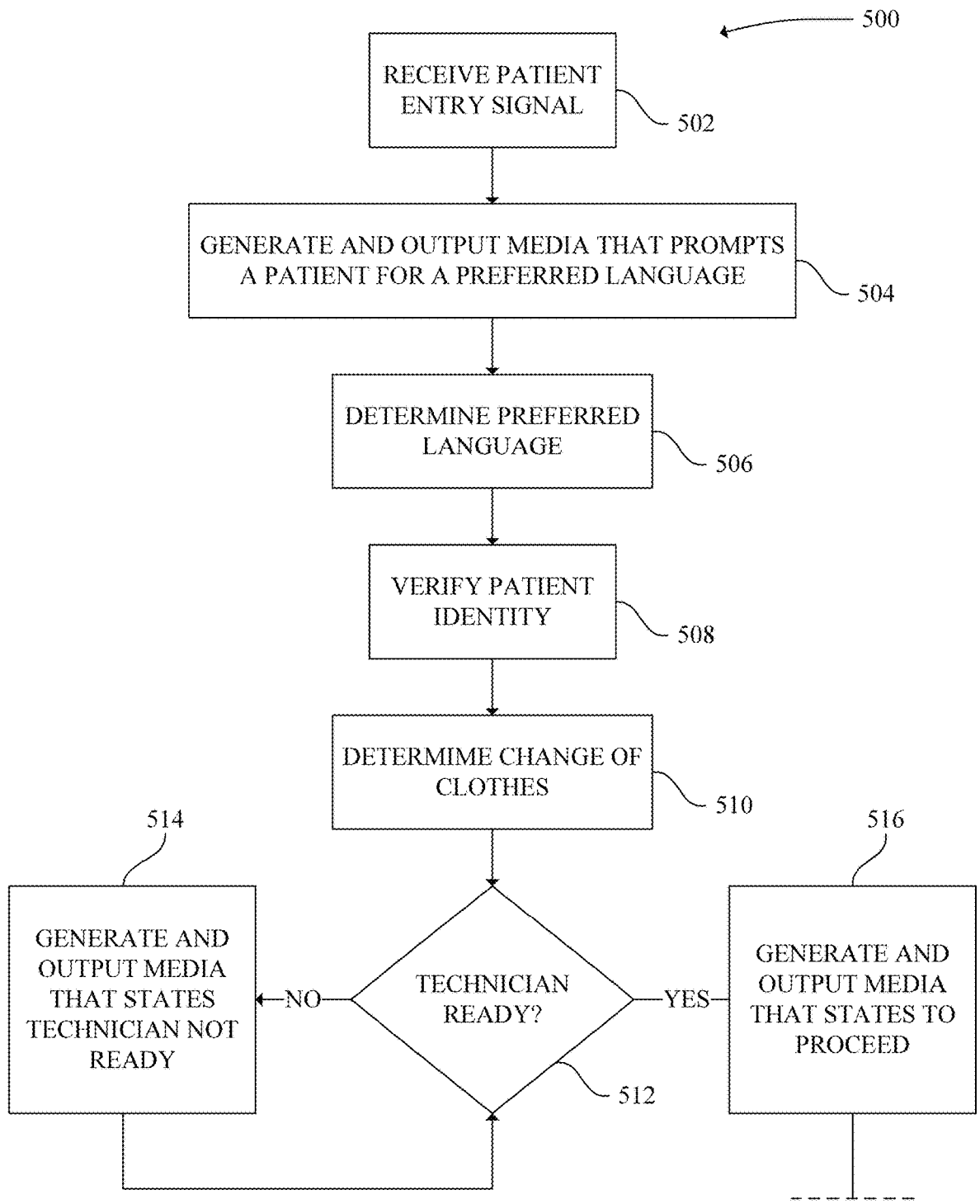
FIG. 5A is a flow chart of a method for augmenting patient-technologist communication in accordance with an exemplary embodiment.
Figure 5B:
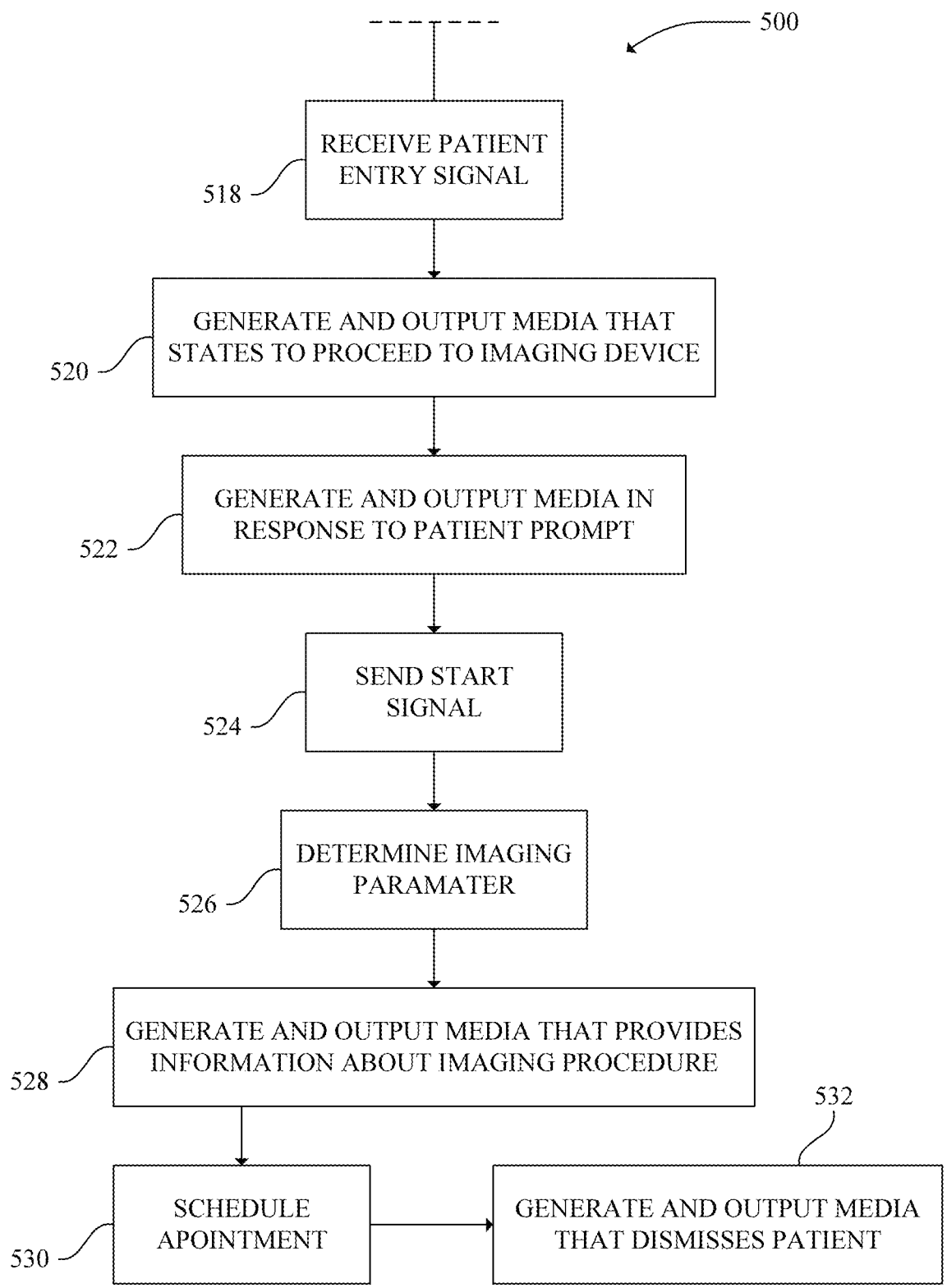
FIG. 5B is a flow chart of a method for augmenting patient-technologist communication in accordance with an exemplary embodiment.
Figure 7:
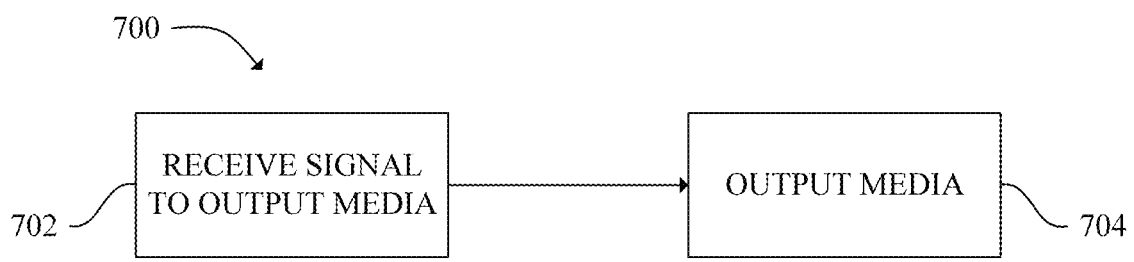
FIG. 7 is a flow chart of a method for answering questions and/or providing instructions to a patient in accordance with an exemplary embodiment.

Referring to FIGS. 5A and 5B a flow chart of a method 500 for augmenting patient-technologist communication is shown in accordance with an exemplary embodiment. For the sake of clarity, FIG. 5A depicts steps 502-516 of the method 500 and FIG. 5B depicts steps 518-532 of the method 500. Various aspects of various methods herein may be carried out by a "configured processor." As used herein, a configured processor is a processor that that is configured according to an aspect the present disclosure. A configured processor(s) may be in computer system 216, one or more nodes 302, and/or a device 304. A configured processor executes various computer readable program instructions to perform the steps of the method 500 and the method 700 (FIG. 7). The computer readable program instructions, that when executed by a configured processor cause the configured processor to carry out the steps of the method 500 and 700 may be stored in the system memory 414. The technical effect of the method 500 is augmenting patient-technologist communication.

At 502, the configured processor receives a signal that is indicative of the patient 114 entering the changing room 100 from first sensor 102. The first sensor 102 detects the patient 114 has entered the changing room 100 and in response sends the signal to the configured processor. In one example, wherein the first sensor 102 is a motion detector, the first sensor 102 detects the patient 114 has entered the changing room 100 by detecting motion in the changing room 100. In another example, wherein the first sensor 102 is a pressure sensor within the floor of the changing room 100, the first sensor 102 detects the patient 114 has entered the changing room 100 by detecting pressure applied to the first sensor 102.

At 504, in response to receiving the signal indicative of the patient 114 entering the changing room 100, the configured processor generates and outputs media to the first display 104 and/or the first speaker 106. The media introduces the configured processor as a virtual assistant and notifies the patient 114 that the patient 114 may communicate with the virtual assistant to ask or answer questions. When introducing the virtual assistant, the media may include a name of the virtual assistant. For example, the media that introduces the virtual assistant may include "hello, my name is Aida." When notifying the patient 114 that the patient 114 may communicate with the virtual assistant, the media may notify the patient 114 that the patient 114 must first say a keyword. For example, the media that notifies the patient 114 that the patient 114 may communicate with the virtual assistant may include "if you have a question for me, ask me by first saying my name." The media also prompts the patient 114 for a preferred language in one or more languages. In one example, the media that prompts the patient 114 for a preferred language may include "what language would you like to proceed in?" In another example, the media that prompts the patient 114 for a preferred language may include "para Espanola, habla Espanol" which means for Spanish, say Spanish.

At 506, the configured processor determines a language the patient 114 prefers. The configured processor determines the preferred language as a function of audio that indicates the patient's 114 preferred language.

The first microphone 108 captures the audio that indicates the patient's 114 preferred language and sends the audio to the configured processor while or after the configured processor generates and outputs the media at 504. As described in further detail herein, the configured processor generates and outputs additional media at various points in the method 500. The additional media is generated and output in the determined preferred language. While the additional media is described as in English, the additional media may be in any language. In one example, the audio that indicates the patient's 114 preferred language may include "I'd like to continue in English." In this example, the configured processor determines the preferred language is English and proceeds to generate and output additional media in English. In another example, the audio that indicates the patient's 114 preferred language may include "Espanol." In this example the configured processor determines the preferred language is Spanish and proceeds to generate and output additional media in Spanish.

At 508, the configured processor verifies the identity of the patient 114 as a patient scheduled for a medical imaging procedure within a threshold period (i.e., within 5, 10, 15 minutes, etc.) form a current time.

In one embodiment the configured processor verifies the identity of the patient 114 as a function of an image/video captured by the first sensor 102 and an image associated with an EMR. The first sensor 102 captures and sends an image/video to the configured processor after the first sensor 102 detects the patient 114 has entered the changing room 100. In this embodiment, the configured processor accesses and analyses a schedule to determine a patient identity that is scheduled for an imaging procedure at or near a current time. The configured processor then accesses an EMR within the EMR database that corresponds to the determined scheduled patient identity. The configured processor then compares the image/video captured by the first sensor 102 to an image associated with the accessed EMR. The configured processor analyzes the images/video and image with facial recognition software and verifies the identity of the patient 114 as the scheduled patient when the configured processor determines the images/video and image include a same person.

For example, at 2:57 PM the first sensor 102 captures an image of the patient 114 and sends the image to the configured processor. The configured processor then analyses a schedule and determines John Doe is scheduled for a CT scan at 3:00 PM. The configured processor then accesses an EMR corresponding to John Doe and compares an image associated with John Doe's EMR with the image captured by the first sensor 102. In this example, the configured processor determines the patient 114 in the captured image matches the person in a photo associated with John Doe's EMR. Accordingly, the configured processor verifies the identity of the patient 114 as the patient scheduled for a medical imaging procedure.

In another embodiment the configured processor verifies the identity of the patient 114 as a function of audio that identifies the patient 114. The first microphone 108 captures the audio that identifies the patient 114 while or after the configured processor generates media that asks the patient 114 a verification question and outputs the media to the first display 104 and/or the first speaker 106. The configured processor generates the verification question as a function of information within an EMR and/or a schedule. The configured processor accesses and analyzes a schedule to determine a patient identity that is scheduled for a medical procedure at or near a current time. The configured processor then obtains information (i.e., name, date of birth, reason for visit, etc.) from the schedule or an EMR that corresponds to the determined scheduled patient identity. The configured processor compares the information in the audio that identifies the patient to the obtained information and verifies the identity of the patient 114 as the scheduled patient when obtained information matches the information in the audio.

For example, at 3:07 the configured processor analyzes a schedule and determines Jane Doe is scheduled for an MRI at 3:00 and further analyzes an EMR corresponding to Jane Doe and determines Jane Doe's date of birth is Nov. 7, 1990. The configured processor may generate and output media that includes "can you please tell me your name and date of birth?" as the configured processor has determined the name and date of birth of the patient scheduled for a 3:00 PM medical imaging procedure. In this example, the captured audio may include "my name is Jane Doe and my date of birth is Nov. 7, 1990." Accordingly, the configured processor verifies the identity of the patient 114 as the patient scheduled for a medical imaging procedure.

At 510, the configured processor determines the clothes the patient 114 needs to change into. The configured processor determines the clothes the patient 114 needs to change into as a function of information (i.e., type of medical imaging procedure, location of medical imaging procedure, etc.) in a schedule and/or an EMR that corresponds to the patient 114.

In one example, the configured processor may analyze an EMR that corresponds to the patient 114 and may determine the patient 114 is to undergo a chest CT scan. As such, the configured processor determines the patient 114 should remove only their shirt and should change into a medical gown. In another example, the configured processor may analyze a schedule and determine that the patient 144 is to undergo a leg X-ray. As such, the configured processor determines the patient 114 should change into medical exam shorts and should not change their shirt.

Furthermore, at 510, the configured processor generates media as a function of the determined change of clothes and outputs the media to the first display 104 and/or the first speaker 106. The media generated as a function of the determined change of clothes notifies the patient 114 what to change into. In one example, wherein the configured processor determines the patient 114 should remove only their shirt and put on a medical gown, the media that notifies what the patient 114 should change into may include "for this procedure, you will need to remove your shirt and put on a medical gown. You may leave your pants on." In another example, wherein the configured processor determines the patient 114 should change into medical exam shorts the media that notifies the patient 114 should change into may include "you need to change into medical exam shorts. Please do not change your shirt."

Also, at 510, the configured processor generates and outputs media that instructs the patient 114 to proceed to the changing closet 112 where the patient 114 will find a change of clothes and instructs the patient 114 to notify the virtual assistant when the patient 114 has finished changing. The configured processor outputs this media to the first display 104 and/or the first speaker 106. In some embodiments while or after the configured processor outputs the media that asks the patient 114 to proceed to the changing closet 112, the configured processor sends a signal to the first projector 110 to illuminate a path to the changing closet 112 and/or to illuminate the changing closet 112. In response to receiving the signal to illuminate a path to the changing closet 112 and/or to illuminate the changing closet 112, the first projector 110 illuminates a path to the changing closet 112 and/or illuminates the changing closet 112. In one example, the media that asks the patient 114 to proceed to the changing closet 112 may include "please proceed to the changing closet. I have illuminated a path to the closet for you to follow. Let me know when you are done changing."

At 512, in response to determining the patient 114 is ready to proceed, the configured processor determines whether the technologist 220 is ready to proceed. The configured processor determines the patient 114 is ready to proceed as a function of audio that indicates the patient 114 is ready to proceed. The first microphone 108 captures the audio that indicates the patient 114 is ready to proceed while or after the configured processor generates and outputs the media at 510. For example, audio that indicates the patient 114 is ready to proceed may include "I'm done changing."

In response to determining the patient 114 is ready to proceed, the configured processor generates media that asks the technologist 220 if the technologist 220 is ready to proceed and outputs the media to at least one of the second display 204, the second speaker 206, a display of the computer system 216 and a speaker of the computer system 216. In one example, the media that asks the technologist 220 if the technologist 220 is ready to proceed may include "are you ready for the patient?"

In one embodiment, the configured processor determines whether the technologist 220 is ready to proceed as a function of a signal indicating whether the technologist 220 is ready to proceed. In this embodiment, a GUI displayed by a display of the computer system 216 includes a "yes" and a "no" icon. A computer processor of the computer system 216 generates the signal indicating whether the technologist 220 is ready to proceed in response to the technologist 220 selecting the "yes" or "no" icon and sends the generated signal to the configured processor. The processor of the computer system 216 generates and sends a signal indicating the technologist 220 is ready to proceed in response to the technologist 220 selecting the "yes" icon. The processor of the computer system 216 generates and sends a signal indicating the technologist 220 is not ready to proceed in response to the technologist 220 selecting the "no" icon.

In another embodiment, the configured processor determines whether the technologist 220 is ready to proceed as a function of audio indicating whether the technologist 220 is ready to proceed. The second microphone 208 and/or a microphone of the computer system 216 captures the audio that indicates whether the technologist 220 is ready to proceed while or after the configured processor generates and outputs the media that asks the technologist 220 if they are ready to proceed. In one example, the audio that indicates whether the technologist 220 is ready to proceed includes "yes." In this example, the configured processor determines the technologist 220 is ready to proceed. In another example, the that indicates whether the technologist 220 is ready to proceed includes "I'm not ready." In this example, the configured processor determines the technologist 220 is not ready to proceed.

At 514, in response to determining the technologist 220 is not ready to proceed, the configured processor generates and outputs media that notifies the patient 114 that the technologist 220 is not ready to proceed. In some embodiments, at 514, the configured processor may also generate and output media that provides the patient 114 with information about the medical imaging procedure. The configured processor outputs the media to the first display 104 and/or the first speaker 106. The configured processor may generate the media that provides the patient 114 with information about the medical imaging procedure as a function of information (i.e., type of medical imaging procedure, location of medical imaging procedure, etc.) in an EMR corresponding to the patient 114 and/or a schedule. In one example, the configured processor may analyze an EMR that corresponds to the patient 114 and may determine that the patient 114 is to undergo a PET scan of the brain. In this example, the media that provides more information about the medical imaging procedure may include a video that describes PET scan of the brain. In another example, the configured processor may analyze a schedule and may determine the patient 114 is to undergo an MM scan. In this example, the media that provides more information about the medical imaging procedure may include audio that describes an MM scan.

After a threshold period of time (i.e., 3, 5, 7 minutes, etc.) from determining the technologist 220 is not ready to proceed, the configured processor again determines whether the technologist 220 is ready to proceed at 512.

At 516, in response to determining the technologist 220 is ready to proceed, the configured processor generates media that notifies the patient 114 that the technologist 220 is ready and instructs the patient 114 to enter the imaging room 200. The configured processor outputs the media to the first display 104 and/or the first speaker 106. In one example, the media includes "please proceed to the imaging room." In another example the media includes "the technologist is ready for you now. Please enter the imaging room." Furthermore, at 520, the configured processor may send a signal to the first projector 110 to illuminate a path to the imaging room 200 while or after the configured processor generates and outputs the media. In response to receiving the signal to illuminate a path to the medical imaging room 200, the first projector 110 illuminates a path to the medical imaging room 200.

Referring now to FIG. 5B, at 518, the configured processor receives a signal that is indicative of the patient 114 entering the imaging room 200. The second sensor 202 detects the patient 114 has entered the imaging room 200 and in response sends the signal to the configured processor. The second sensor 202 detects the patient 114 has entered the imaging room 200 in a same or similar manner as discussed at 502 with respect to the first sensor 102 determining the patient 114 entered the changing room 100.

At 520, in response to receiving the signal indicative of the patient 114 entering the imaging room 200, the configured processor generates and outputs media that instructs the patient 114 to proceed to the medical imaging device 212 and instructs the patient 114 to position themselves relative to the medical imaging device 212 in a particular manner. The configured processor outputs this media to the second display 204 and/or the second speaker 206. The configured processor generates the media that instructs the patient 114 to proceed to the medical imaging device 212 and instructs the patient 114 to position themselves relative to the medical imaging device 212 in a particular manner as a function of information (i.e., type of medical imaging procedure, location of medical imaging procedure, etc.) in a schedule and/or an EMR.

In one example, the configured processor may analyze an EMR that corresponds to the patient 114 and may determine the patient 114 is to undergo an MRI that requires the patient 114 to lay down on a bed of the medical imaging device 212 and raise their arm above their head. In this example, the media that instructs the patient 114 to position themselves relative to the medical imaging device 212 in a particular manner may include "please lay down on the bed with your head on the pillow and raise your right arm above your head." In another example, the configured processor may analyze a schedule and may determine that the patient 114 is to undergo a leg X-ray that requires the patient 114 to stand in front of and face the medical imaging device 212. In this example, the media that instructs the patient 114 to position themselves relative to the medical imaging device 212 in a particular manner may include "please stand in front of and face the X-ray machine."

While or after the configured processor outputs the media that instructs the patient 114 to position themselves relative to the medical imaging device 212 in a particular manner, the configured processor may send a signal to the second projector 210 to illuminate a path to the medical imaging device 212 and/or to illuminate a proper patient position. In response to receiving the signal to illuminate a path to the medical imaging device 212 and/or to illuminate a proper patient position, the second projector 210 illuminates a path to the medical imaging device 212 and/or illuminates a proper patient position.

At 522, in response to a patient 114 prompt, the configured processor generates and outputs media that includes a response to the patient 114 prompt. When the prompt includes a question, the media that includes a response to the prompt includes an answer to the question. The configured processor may generate the media that includes a response to a patient 114 prompt as a function of information (i.e., type of medical imaging procedure, location of medical imaging procedure, length of medical imaging procedure, typical imaging procedure experiences, etc.) within a schedule, EMR associated with the patient 1114, and/or on the internet. The configured processor outputs this media to the second display 204 and/or the second speaker 206. The second microphone 208 captures the audio that includes the prompt after the patient 114 says a keyword. The second microphone 208 then sends this audio to the configured processor.

In one example, the prompt may include "Aida, how long will this take?" In this example the configured processor may analyze a schedule (as a schedule may include how long the imaging procedure for the patient 114 will take) and may determine the imaging procedure will take 15 minutes. In this example, the media may include "your scan will take 15 minutes." In another example the prompt may include "Aida, will this hurt?" In this example, the configured processor may analyze an EMR associated with the patient 114 and may determine the patient 114 will be undergoing a CT scan of the chest. The configured processor may search the interne and determine that a CT scan of the chest is painless. As such, the media includes "a CT scan is a painless procedure."

While FIG. 5B depicts the configured processor as generating and outputting media that includes a response to a patient 114 prompt at 522, the configured processor may generate and output this media at any point in the method 500. When the patient 114 prompts the virtual assistant a question while in the changing room 100, the first microphone 108 captures and sends the audio to the configured processor.

At 524, the configured processor sends a start signal to the medical imaging device 212. In response to receiving the start signal, the medical imaging device 212 begins the medical imaging procedure.

In one embodiment, the configured processor sends the start signal in response to receiving a signal that enables the configured processor to control the imaging device 212. The computer system 216 generates and sends the signal that enables the configured processor to control the imaging device 212 to the configured processor in response to the technologist 220 selecting a "start" icon or the like displayed in a GUI of the computer system 216. In another embodiment, the configured processor sends the start signal to the imaging device 212 as a function of audio that enables the configured processor to control the medical imaging device 212. In this embodiment, while or after the configured processor outputs media that prompts the technologist 220 to start the medical imaging procedure, the second microphone 208 and/or a microphone of the computer system 216 captures and sends audio that enables the configured processor to control the imaging device 212 to the configured processor. For example, the audio that enables the configured processor to control the imaging device 212 may include "start scan."

At 526, the configured processor determines an imaging parameter and sends a signal indicative of the imaging parameter to the imaging device 212. In response to receiving the signal indicative of an imaging parameter, the imaging device 212 modifies or sets an imaging parameter as a function of the signal. Furthermore, at 526, the configured processor may generate and output media that prompts the patient 114 or the technologist 220 for an imaging parameter. The configured processor outputs this media to at least one of the second display 204, the second speaker 206, a display of the computer system 216, and/or a speaker of the computer system 216.

In one embodiment, the configured processor determines an imaging parameter as a function of audio that indicates the imaging parameter. The second microphone 208 and/or a microphone of the computer system 216 may capture the audio that indicates the imaging parameter while or after the configured processor generates and outputs the media.

In one instance, the media may prompt the patient 114 for an imaging parameter. For example, the patient 114 may be required to hold their breath during an imaging procedure and a default imaging acquisition period may be 30 seconds as some people may be able to hold their breath for at least 30 seconds. In this example, the media that prompts the patient 114 for a modified imaging parameter may include "how long can you hold your breath?" While or after the configured processor outputs this media, the configured processor receives audio from the second microphone 208 that includes "for about 15 seconds." As such, the configured processor determines an image acquisition period as 15 seconds and sends a signal indicative of a 15 second acquisition period to the imaging device 212.

In another instance, the media may prompt the technologist 220 for an imaging parameter. For example, the media that prompts the technologist 220 for an imaging parameter may include "modify imaging parameters?" While or after the configured processor outputs this media, the configured processor receives audio from the second microphone 208 that includes "set acquisition period to 10 seconds." In this example, the configured processor determines an image acquisition period as 10 seconds and sends a signal indicative of a 10 second acquisition period to the imaging device 212.

In yet another instance, after the patient 114 or the technologist 220 says a keyword, the second microphone 208 and/or a microphone of the computer system 216 captures audio that indicates the imaging parameter. In one example, a scan may require a patient to remain in a position for a period of time. In this example, the patient 114 may say "Aida, I can only hold my arm above my head for 5 seconds." The second microphone 208 captures and sends this audio to the configured processor. In this example, the configured processor determines an image acquisition period as 5 seconds and sends a signal indicative of a 5 second acquisition period to the imaging device 212. In yet another example, the technologist 220 may say "Aida, set the image acquisition period to 45 seconds." In this example, the second microphone 208 or a microphone of the computer system 216 captures and sends this audio to the configured processor. In this example, the configured processor determines an image acquisition period as 45 seconds and sends a signal indicative of a 45 second acquisition period to the imaging device 212.

In yet another embodiment, the configured processor determines an imaging parameter as a function of a signal from the computer system 216 that indicates a selected imaging parameter. In this embodiment, the media that prompts the technologist 220 for an imaging parameter may be displayed in a GUI of a display of the computer system 216. The GUI may also display one or more icons that correspond to imaging parameters. In response to the technologist 220 selecting one of the icons, the computer system 216 sends a signal that indicates the selected imaging parameter to the configured processor. For example, the GUI may display an icon that states "60 second acquisition period." In response to the technologist 220 selecting this icon, the computer system 216 sends a signal that indicates a 60 second imaging acquisition period to the configured processor. In this example, the configured processor determines an image acquisition period as 60 seconds and sends a signal indicative of a 60 second acquisition period to the imaging device 212.

In yet another embodiment, the configured processor determines an imaging parameter as a function of biometric data. In this embodiment, the third sensor 214 captures and sends biometric data to the configured processor. In one example, the patient 114 may have to hold their arm above their head for 45 seconds. During this time the third sensor 214 may capture an image of the patient 114 and may send this image to the configured processor. The configured processor may analyze this image and may determine the patient's 114 facial expression indicates the patient 114 is in pain. As such, the configured processor may determine the image acquisition period as 30 seconds as this will require the patient 114 to hold their arm above their head, which may be the cause of the patient's 114 pain, for a shorter period of time. The configured processor then sends a signal indicative of a 30 second acquisition period to the imaging device 212. In another example, the third sensor 214 may capture a heart rate of the patient 114 and may send the captured heart rate to the configured processor. If the configured processor determines the heart rate is above a threshold (i.e., 125 beats per minute (bpm), 130 bpm, 140 bpm, etc.) then the configured processor may determine a shorter image acquisition period as a shorter image acquisition period may cause the patient 114 to relax thereby lowering their heart rate. In this example, an imaging acquisition period is set to 5 minutes and the configured processor determines the patient's 114 heart rate is above the threshold. In this example, the configured processor determines an image acquisition period as 4 minutes and sends a signal indicative of a 4-minute image acquisition period to the imaging device 212.

At 528, the configured processor generates and outputs media that provides the patient 114 with information about the medical imaging procedure. The configured processor generates this media as a function of an imaging protocol and outputs this media to the second display 204 and/or the second speaker 206. The media that provides the patient 114 with information about the medical imaging procedure may notify the patient 114 of typical experiences associated with the medical imaging procedure and may notify the patient 114 about the progress of the medical imaging procedure.

In one example, the configured processor may analyze an imaging protocol stored in the computer system 216, a node 302, or device 304 and may determine that imaging device 212 has captured two of three images needed to complete the scan. In this example, the media that provides the patient 114 with information about the medical imaging procedure may include "we need to capture one more image." In another example, the configured processor may analyze an imaging protocol stored in the computer system 216, a node 302, or device 304 and may determine that the patient 114 will be undergoing an MIll that may have a loud noise associated with image acquisition. In this example, the media that provides the patient 114 with information about the medical imaging procedure may include "you will hear some loud noises, these noises are normal."

While FIG. 5B depicts the configured processor as generating and outputting media that provides the patient 114 with information about the medical imaging procedure at 528, the configured processor may generate and output this media at any point in the method 500. When the configured processor generates and outputs this media while the patient 114 is in the is in the changing room 100, the first display 104 and/or the first speaker 106 output the media that provides the patient 114 with information about the medical imaging procedure.

At 530, in response to determining the imaging procedure is complete, the configured processor generates and outputs media that prompts the patient 114 to schedule an appointment. The configured processor determines the imaging procedure is complete as a function of a signal indicating that the imaging procedure is complete. After completing an imaging protocol, the imaging device 212 or the computer system 216 may send the signal indicating the imaging procedure is complete to the configured processor. The configured processor may generate the media that prompts the patient 114 to schedule an appointment as a function of information within an EMR associated with the patient 114 and/or a schedule. The configured processor may output the media that prompts the patient 114 to schedule an appointment to one of the first display 104, the first speaker 106, the second display 204, and/or the second speaker 206.

For example, after determining the imaging procedure is complete, the configured processor may analyze an EMR associated with the patient 114 and may determine that the patient 114 needs to see a physician to review the results of the medical imaging procedure and may analyze a schedule to determine that the physician is available on Monday June 17$^{th}$ at 2:00 P.M. In this example, the media that prompts the patient 114 to schedule an appointment may include "I see you need to come back to review your images, does June 17$^{th}$ at 2:00 P.M. work for you?"

Furthermore, at 530, the configured processor schedules an appointment for the patient 114 as a function of audio indicating to schedule the appointment. While or after the configured processor generates and outputs the media that prompts the patient 114 to schedule an appointment, the first microphone 108 or the second microphone 208 capture and sends audio that indicates to schedule an appointment. For example, the audio that indicates to schedule an appointment may include "June 17$^{th}$ at 2 P.M. works." In this example, the configured processor schedules an appointment for the patient 114 on June 17$^{th}$ at 2:00 P.M.

At 532, the configured processor generates and outputs media that dismisses the patient 114. Furthermore, at 532, the configured processor sends a signal to the second projector 210 to illuminate a path to the exit of the imaging room 200 and sends a signal to the the first projector 110 to illuminate a path to the changing closet 112. The first projector 110 and the second projector 210 illuminate their respective paths in response to receiving the signal to illuminate the paths. The media that dismisses the patient 114 may include "your imaging procedure is complete; I have illuminated a path to the exit and a path to the closet where you will find your change of clothes."

Figure 6:
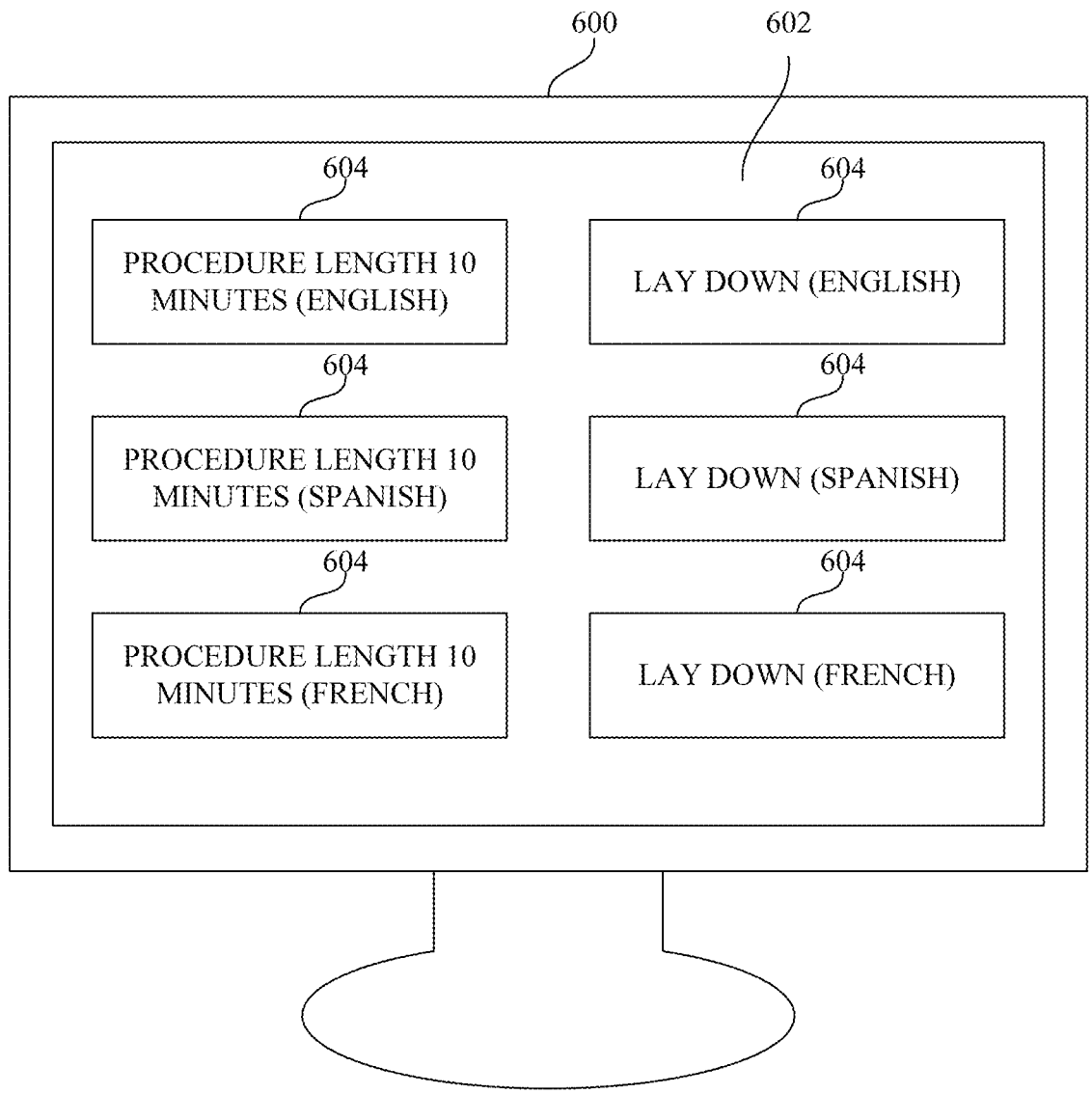
FIG. 6 is a display with a graphical user interface in accordance with an exemplary embodiment.

Referring to FIG. 6, a display 600 with a GUI 602 is shown in accordance with an exemplary embodiment. The GUI 602 is generated and output by a configured processor of a computer system. The display 600 may be a display of the computer system 216. the technologist 220 may interact with the GUI 602 via an input device (i.e., a mouse, keyboard, etc.).

As shown in FIG. 6, in some embodiments, the GUI 602 displays one or more icons 604. The icons 604 are selectable and correspond to a media file. The corresponding media file is stored in a computer readable storage medium that may be connected to a node 302 or a device 304. The icons 604 may state an instruction (i.e., patient positioning, patient dismissal, etc.), information relating to a medical imaging procedure (i.e., procedure length, time remaining in procedure, type of medical procedure, etc.) and may state a language of the corresponding media file. In one example an icon 604 may read "procedure length, 10 minutes (English) ." In another example, an icon 604 may read "lay down, (Spanish)." While the icons 604 depicted in FIG. 6 display and correspond to an English, Spanish, and French procedure length and instruction to lay down, it is understood that the icons 604 may display and correspond any information and any instruction that relates to a medical imaging procedure in any language.

Referring to FIG. 7 a flow chart of a method 700 for answering questions and/or providing instructions to the patient 114 before, during, or after a medical imaging procedure is shown in accordance with an exemplary embodiment. The technical effect of the method 700 is augmenting patient-technologist communication.

At 702, a configured processor receives a signal to retrieve and output media that includes instructions or information relating to a medical imaging procedure. The signal indicates corresponds to specific media stored in a node 302 or a device 304 the media may be in different languages. The configured processor receives the signal indicating to retrieve and output media from the computer system 216. A display of the computer system 216 displays the GUI 602 with a plurality of icons 604. Each icon 604 corresponds to media stored in a node 302 or a device 304 and a language of the media. The technologist 220 uses a mouse or another external device connected to the computer system 216 to select and click one of the icons 604. In response, the computer system 216 generates and sends the signal to retrieve and output media to the configured processor.

In one example, in order to begin a medical procedure, the patient 114 may have to lay down on a bed of the imaging device 212. In this example, the technologist 220 may use a mouse of the computer system 216 to select an icon 604 in the GUI 602 that states "please lay down (English)." In response to the technologist 220 selecting this icon 604, the computer system 216 generates and sends a signal to retrieve and output media corresponding to the "please lie down (English)" icon 604. In another example, after completing the medical imaging procedure, the technologist 220 may use a mouse of the computer system 216 to select an icon

604 in a that states "dismiss patient, (Spanish)." In response to the technologist 220 selecting this icon 604, the computer system 216 generates and sends a signal to retrieve and output media corresponding to the "dismiss patient (Spanish)" icon 604.

At 704, the configured processor retrieves and outputs media as a function of the received signal. When the media includes visual text, the first display 104 and/or the second display 204 display the media. When the media includes audio, the first speaker 106 and/or the second speaker 206 emit the audio. In one example, the received signal indicates the configured processor should retrieve and output media corresponding to a "please lie down (English)" icon 604. In this example, the configured processor retrieves and outputs corresponding media. The corresponding media media may include "please lay down on the bed" in English. In another example, the received signal indicates the configured processor should retrieve and output media corresponding to a "dismiss patient (Spanish)" icon 604. In this example, the configured processor retrieves and outputs the corresponding media. The corresponding media may include "the exam has ended" in Spanish.

In addition to any previously indicated modification, numerous other variations and alternative arrangements may be devised by those skilled in the art without departing from the spirt and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments are meant to be illustrative only and should not be construed to be limiting in any manner.

What is claimed is:

1. A system comprising:
   a processor;
   a computer readable storage medium in communication with the processor, wherein the processor executes program instructions stored in the computer readable storage medium which cause the computer processor to:
   generate a graphical user interface comprising:
   a plurality of icons that each correspond to a media file stored in a computer readable storage medium,
   wherein each icon displays information or an instruction relating to a medical imaging procedure, and
   wherein the media file includes information or instructions that corresponds to the displayed information or instruction;
   output the graphical user interface to a first display in a first location; and
   output the media file that corresponds to an icon to a speaker in a second location with a patient in response to a technologist in the first location selecting the icon, wherein the media file includes a prompt for the patient.

2. The system of claim 1, wherein a set of icons in the plurality of icons displays a same instruction and a language, and wherein the language displayed in each of the icons in the set of icons corresponds to a language of the media file that corresponds to each icon.

3. The system of claim 1, wherein the media file is stored in a node of a cloud computing environment.

\* \* \* \* \*